(12) United States Patent
Reyes et al.

(10) Patent No.: US 12,706,213 B1
(45) Date of Patent: Aug. 11, 2026

(54) SYSTEM OF USING ARTIFICIAL INTELLIGENCE IN CANINE RADIOGRAPHY

(71) Applicants: Tomas Reyes, Bryan, TX (US); Tabitha Baibos, Bryan, TX (US)

(72) Inventors: Tomas Reyes, Bryan, TX (US); Tabitha Baibos, Bryan, TX (US)

(73) Assignee: Rod Analyzer LLC, Austin, TX (US)

(*) Notice: Subject to any disclaimer, the term of this patent is extended or adjusted under 35 U.S.C. 154(b) by 330 days.

(21) Appl. No.: 18/196,355

(22) Filed: May 11, 2023

Related U.S. Application Data

(60) Provisional application No. 63/341,102, filed on May 12, 2022.

(51) Int. Cl.

| | |
|---|---|
| ***G16H 50/20*** | (2018.01) |
| ***G06T 7/00*** | (2017.01) |
| ***G06T 7/90*** | (2017.01) |

(52) U.S. Cl.
CPC .......... *G16H 50/20* (2018.01); *G06T 7/0012* (2013.01); *G06T 7/90* (2017.01); *G06T 2207/10024* (2013.01); *G06T 2207/10116* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC ......... G16H 50/20; G06T 7/90; G06T 7/0012; G06T 2207/10024; G06T 2207/10116; G06T 2207/20081; G06T 2207/20084; G06T 2207/30048; G06T 2207/30101
See application file for complete search history.

(56) References Cited

U.S. PATENT DOCUMENTS

| | | | | |
|---|---|---|---|---|
| 2019/0341150 | A1* | 11/2019 | Mostofi | G16H 50/20 |
| 2022/0351854 | A1* | 11/2022 | Li | G16H 30/00 |
| 2022/0383493 | A1* | 12/2022 | Choi | A61B 6/508 |
| 2025/0166824 | A1* | 5/2025 | Taube | G16H 30/40 |

OTHER PUBLICATIONS

Development of Automated Volumetric Analysis of Canine Heart in Thoracic Radiograph Using Deep Learning. Diss. , 2021 (Year: 2021).*
Jeong, "Development of Automated Volumetric Analysis of Canine Heart in Thoracic Radiograph Using Deep Learning", 2021. (Year: 2021).*

* cited by examiner

*Primary Examiner* — Utpal D Shah
(74) *Attorney, Agent, or Firm* — INRI Potest Law, PLLC; Bradley Hankelman

(57) ABSTRACT

A system of using artificial intelligence for vertebral heart scale (VHS) and vertebral left atrial score (VLAS) prediction in canine radiography comprising a canine needing radiography, which is done by one or more veterinarians on a radiography device. The radiography image/s generated by the radiography device are then uploaded on to a digital device running online or mobile application.

20 Claims, 11 Drawing Sheets

1500
Start
1501
Create bounding box with 4 points
1502
Perform tolerance Test with bounding Box area
End 1400
Start
1401
Use AI to check to See if image is Obscured in any way
1402
Return true or false
End 1300
Start
1301
Normalize image
1302
Check to see what Range the value lies Within
1303
Find tolerance from Range
End

SYSTEM OF USING ARTIFICIAL INTELLIGENCE IN CANINE RADIOGRAPHY

BACKGROUND

1. Field of the Invention

The present invention generally relates to radiography, and more specifically to a system of using artificial intelligence for vertebral heart scale (VHS) and vertebral left atrial score (VLAS) prediction in canine radiography and its mobile or online application.

2. Description of Related Art

Radiography is an imaging technique that uses a type of high-energy radiation called X-rays, gamma rays, or similar ionizing radiation and non-ionizing radiation to view the internal form of an object and to take pictures of areas inside the body onto film or a computer. Applications of radiography include medical radiography ("diagnostic" and "therapeutic") and industrial radiography. To create an image in conventional radiography, a beam of X-rays is produced by an X-ray generator and is projected toward the object. A certain amount of the X-rays or other radiation is absorbed by the object, dependent on the object's density and structural composition. The X-rays that pass through the object are captured behind the object by a detector (either photographic film or a digital detector). The generation of flat two-dimensional images by this technique is called projection radiography. In computed tomography (CT scanning) an X-ray source and its associated detectors rotate around the subject which itself moves through the conical X-ray beam produced. Any given point within the subject is crossed from many directions by many different beams at different times. Information regarding the attenuation of these beams is collated and subjected to computation to generate two-dimensional images in three planes (axial, coronal, and sagittal) which can be further processed to produce a three-dimensional image.

Radiography is a vital, yet time-consuming process that requires trained technicians. While these technicians provide an important service, they are not without fault. It has been observed that radiologists generally flag more than 60 percent of the scans they perform to be a 'high priority' when they actually may not be serious at all. Many medical economists believe that imaging is overused; more than 80 million such scans are performed every year in the U.S. alone. For these reasons, the healthcare industry has been employing software to ensure quality control. The application of computer software to enhance radiology scans has been in practice for at least a decade, In the 1990s radiologists employed a program called 'computer-assisted diagnoses' to detect breast cancer in mammograms. The software was considered to be a success and clinics around the United States begin implementing it in their practice, at the same time, it wasn't perfect. In the past decade, however, computer software in the medical field has improved significantly. These improvements have been largely driven by the development of artificial intelligence, in which a computer is given a set of images and then left to draw its connections by developing a network of associations. The enhancement of radiography using Artificial Intelligence (AI) has benefits. For example, physicians working in developing countries might not have access to the same kinds of scanners as a major medical institution in the U.S. or Europe or trained radiologists who can interpret scans. As hospitals become more dependent on image analysis, the gap between the standard of care provided in wealthier and poorer areas is growing. Many agree that the application of AI can be an affordable way to close this gap.

Accordingly, although great strides have been made in the area of radiography, many shortcomings remain.

DESCRIPTION OF THE DRAWINGS

The novel features believed characteristic of the embodiments of the present application is outlined in the appended claims. However, the embodiments themselves, as well as a preferred mode of use, and further objectives and advantages thereof, will best be understood by reference to the following detailed description when read in conjunction with the accompanying drawings, wherein:

Figure 1:
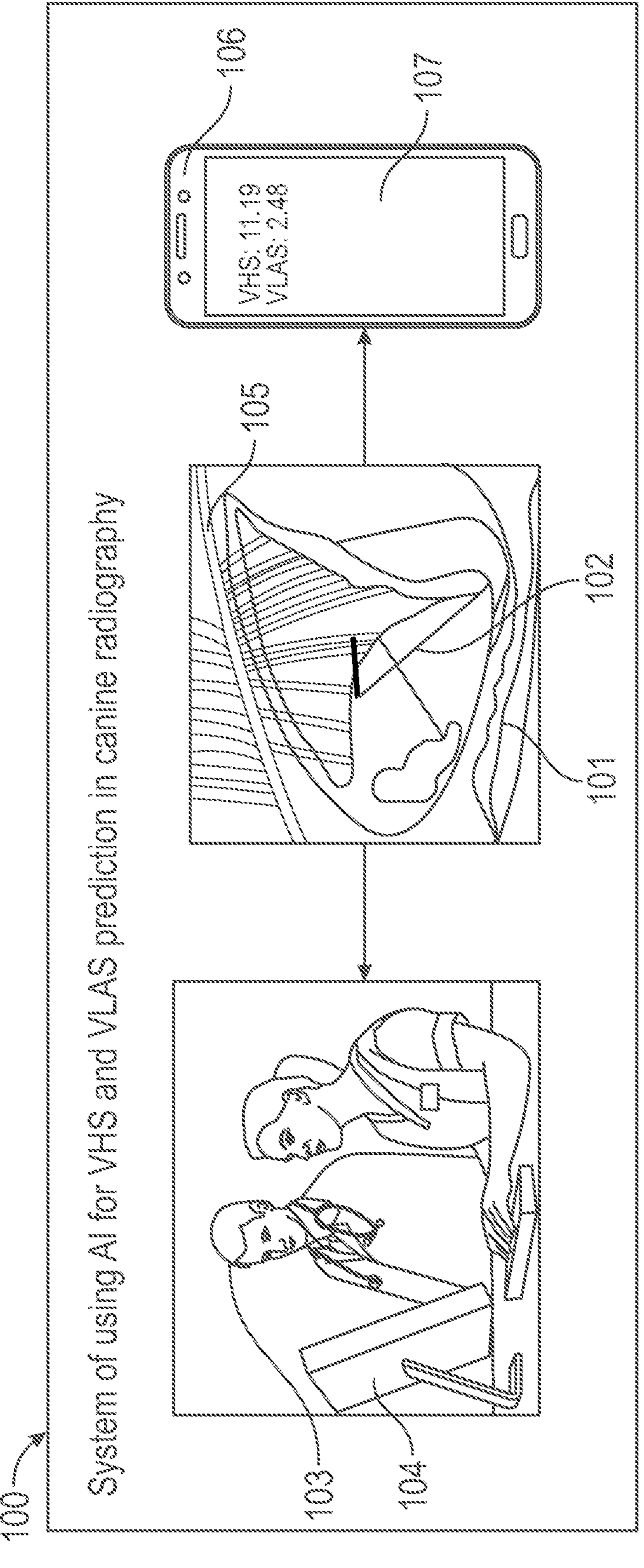
FIG. 1 shows a system of using artificial intelligence for vertebral heart scale (VHS) and vertebral left atrial score (VLAS) prediction in canine radiography.

While the system and method of use of the present application are susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use by the present application overcome one or more of the above-discussed problems commonly associated with conventional radiography. Specifically, the system of using convolutional neural networks (CNNs) and reinforcement learning (RL) for vertebral heart scale (VHS) and vertebral left atrial score (VLAS) prediction in canine radiography by leveraging artificial intelligence (AI) for x-ray analysis and predictions. The system of the present invention can be used to enhance the accuracy and reliability of radiographical interpretations.

These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined and/or interchanged with one another, all of which are within the scope of the present application, even though not all variations and particular embodiments are shown in the drawings. It should also be understood that the mixing and matching of features, elements, and/or functions between various embodiments are expressly contemplated herein so that one of ordinary skill in the art would appreciate from this disclosure that the features, elements, and/or functions of one embodiment may be incorporated into another embodiment as appropriate unless described otherwise.

Canine may refer to a dog-like canid animal in the subfamily caninae including but not limited to dogs, wolves, coyotes, and jackals.

Artificial intelligence (AI) is intelligence demonstrated by machines, as opposed to the intelligence of humans and other animals. Example tasks in which this is done include speech recognition, computer vision, translation between (natural) languages, as well as other mappings of inputs. Machine learning (ML), a fundamental concept of AI research since the field's inception, is the study of computer algorithms that improve automatically through experience.

Artificial intelligence in healthcare is an overarching term used to describe the use of machine-learning algorithms and software, or artificial intelligence (AI), to mimic human cognition in the analysis, presentation, and comprehension of complex medical and healthcare data. Specifically, AI is the ability of computer algorithms to approximate conclusions based solely on input data. The primary aim of health-related AI applications is to analyze relationships between clinical techniques and patient outcomes. AI programs are applied to practices such as diagnostics, treatment protocol development, drug development, personalized medicine, and patient monitoring and care. What differentiates AI technology from traditional technologies in healthcare is the ability to gather data, process it, and produce a well-defined output for the end-user. AI does this through machine learning algorithms and deep learning. These processes can recognize patterns in behavior and create their logic. To gain useful insights and predictions, machine learning models must be trained using extensive amounts of input data.

Machine learning is a branch of artificial intelligence (AI) and computer science that focuses on the use of data and algorithms to imitate the way that humans learn, gradually improving its accuracy.

Reinforcement learning (RL) is a machine learning training method based on rewarding desired behaviors and/or punishing undesired ones. In general, a reinforcement learning agent can perceive and interpret its environment, take actions and learn through trial and error. Reinforcement learning (RL) is concerned with how intelligent agents ought to take action in an environment to maximize the notion of cumulative reward.

Deep learning is part of artificial intelligence (AI) based on artificial neural networks with representation learning. Learning can be supervised, semi-supervised, or unsupervised. Deep-learning architectures can be applied to medical image analysis.

Within Deep Learning, a Convolutional Neural Network (CNN) is a type of artificial neural network, which is widely used for image/object recognition and classification. Deep Learning thus recognizes objects in an image by using a CNN. CNNs are particularly useful for finding patterns in images to recognize objects, classes, and categories. A CNN is a kind of network architecture for deep learning algorithms and is specifically used for image recognition and tasks that involve the processing of pixel data.

Radiography is a procedure that uses a type of high-energy radiation to take pictures of areas inside the body. Radiation passes through the body onto film or a computer, where the pictures are made. It is used to diagnose or treat patients by recording images of the internal structure of the body to assess the presence or absence of disease, foreign objects, and structural damage or anomaly. During a radiographic procedure, an X-ray beam is passed through the body. Radiography includes but is not limited to X-rays, computed tomography (CT), fluoroscopy, and nuclear medicine including positron emission tomography (PET).

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein reference characters identify corresponding or similar elements throughout the several views, FIGS. 1-15 depict a system of using convolutional neural networks and reinforcement learning for VHS and VLAS prediction in canine radiography 100 by a preferred embodiment of the present application. It will be appreciated that said system 100 overcomes one or more of the above-listed problems commonly associated with conventional radiography. In addition, it should be appreciated that more or fewer of such components may be included in different embodiments of the system 100.

The system of using AI for VHS and VLAS prediction in canine radiography 100 comprises a canine 101 needing vertebral heart scale (VHS) and vertebral left atrial score (VLAS) prediction in canine radiography 102, which was done by one or more veterinarians 103 using a radiography device 104. The radiography image/s 105 generated by the radiography device 104 are then uploaded onto a digital device 106 running a mobile or online application 107, as shown in FIG. 1.

Figure 2:
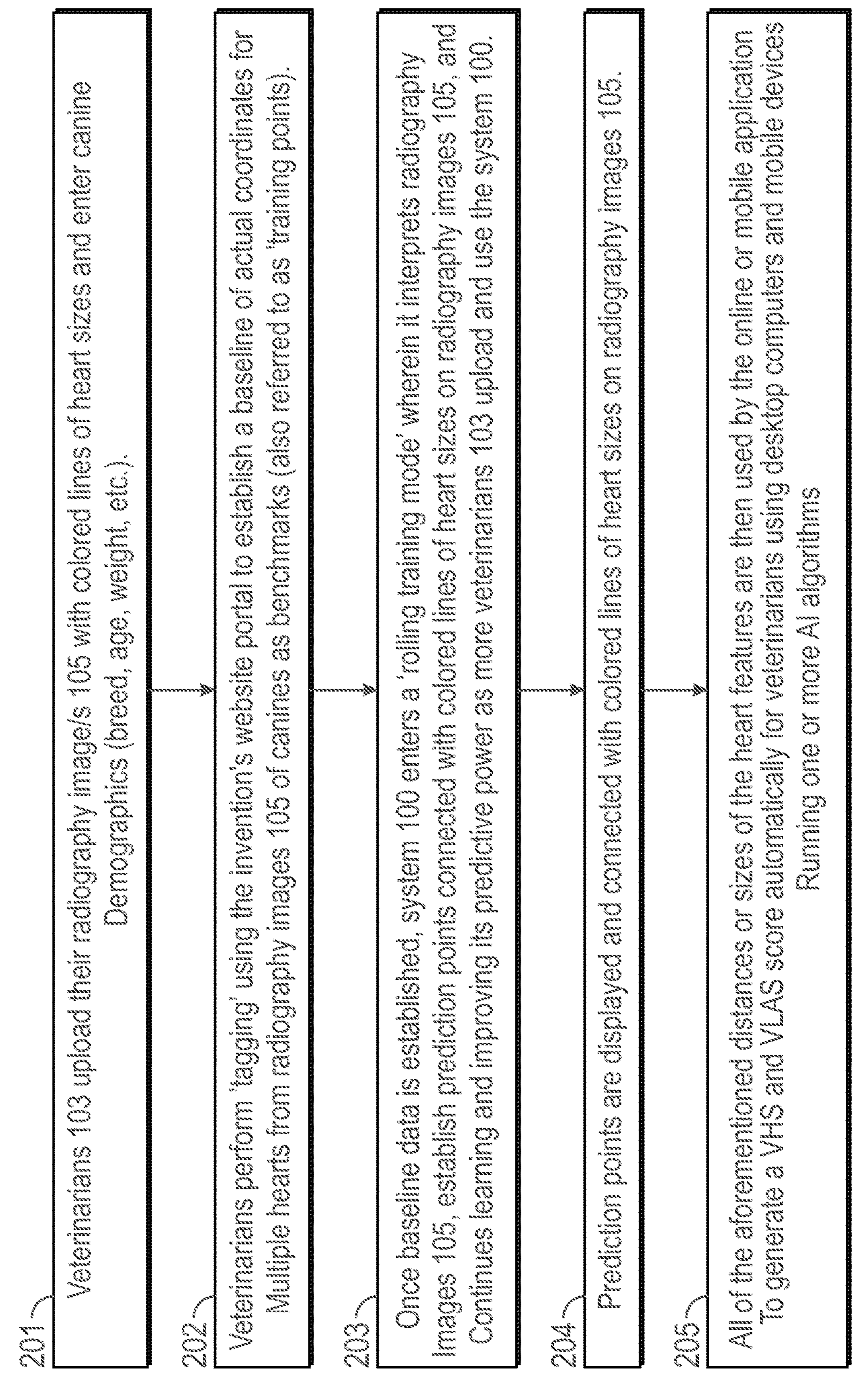
FIG. 2 shows a perspective view of the system displaying prediction lines on an X-ray scan.

The method of use 200 of the system of using AI for VHS and VLAS prediction in canine radiography 100 for displaying prediction points connected with colored lines of heart sizes on radiography images 105 as shown in FIG. 2. The distance of said colored lines represents distances or sizes of the heart features that can include but are not limited to the apex, ventral border, atrium intersection with caudal vena cava, thoracic vertebrae, and the like. In step 201 veterinarians 103 upload their radiography image/s 105 with colored lines of heart sizes and enter canine demographics (breed, age, weight, etc.). In step 202, veterinarians perform 'tagging' using the invention's website portal of the online or mobile application to establish a baseline of actual coordinates for multiple hearts from radiography images 105 of canines as benchmarks (also referred to as 'training points). In step 203, once baseline data is established, system 100 enters a 'rolling training mode' wherein it interprets radiography images 105, establishes prediction points connected with colored lines of heart sizes on radiography images 105, and continues learning and improving its predictive power as more veterinarians 103 upload and use the system 100. In step 204, prediction points are displayed and connected with colored lines of heart sizes on radiography images 105. In step 205, all of the aforementioned distances or sizes of the heart features are then used by the online or mobile application to generate a VHS and VLAS score automatically for veterinarians using desktop computers and mobile devices running one or more AI algorithms.

The AI algorithms include but are not limited to convolutional neural networks (CNN), reinforcement learning (RL), and Deep Learning (DL).

After training, the online or mobile application performs image localization on new x-rays and once an x-ray is uploaded, the AI algorithm/s begin the image localization process on the online or mobile application. The AI algorithm/s first identify specific pixel colors on the image and generates bounding boxes around the points of interest. The image is stored in a grayscale format (a number from 0-255) and by normalizing the image across these values, the program achieves a consistent set of numbers that can allow for pattern comparisons. For example, white inside a normalized X-ray is defined as 1, and a darker area range from 0.0 to 0.99999. CNN performs pattern detection on the images by combining multiple layers with filters ex. edges, shapes, lighting, etc. to detect patterns such as organs and organ locations.

After the CNN process, the RL is performed wherein points are gathered and compared against the benchmarks for accuracy, weighted, and assigned either positive or negative rewards. The RL algorithm interprets grey scale colors on an X-ray and then draws a multitude of lines to define heart measurements. After these lines are applied to the x-ray a 'shaping function' draws a radius around each point to represent the distance to its corresponding benchmark. As the distance (measured in pixels) between this radius and a target point increases, the reward decreases and these points are weighted less by the program.

Conversely, as the distance between the radius and a target point decreases, the reward increases, and these points are weighted more and are used to support a final prediction. They are also placed into the program's library for future scans. Using the bounding boxes from image localization, the program establishes sub-images and generates its own tag points, and draws a line between them to establish distances that predict VHS and VLAS scores for the veterinarian automatically.

Figure 3:
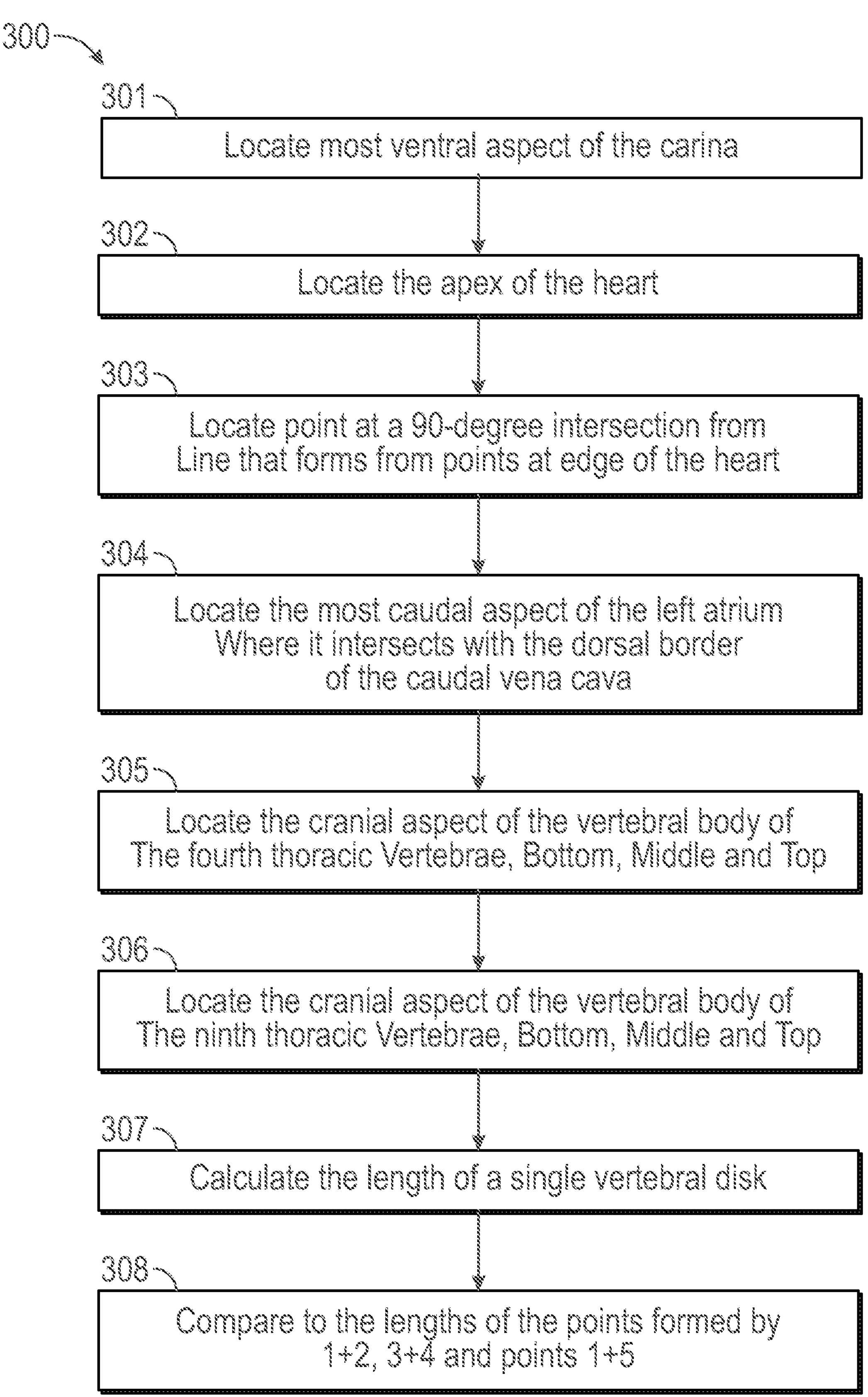
FIG. 3 shows the method steps taken by the system.

FIG. 3 shows the method steps taken by the AI 300 on digital radiography images uploaded into the system. This method includes but is not limited to the following steps: locating the most ventral aspect of the carina and establishing tags; locating the ventral border of the caudal vena cava where it enters the heart and establishing tags in step 301; locating the apex of the heart and establishing tags in step 302; locating the corresponding point 8 that is a 90-degree intersection from the line that forms from points one and two to the edge of the heart and establishing tags in step 303; locating the most caudal aspect of the left atrium where it intersects with the dorsal border of the caudal vena cava and establishing tags in step 304; locating the cranial aspect of the vertebral body of the fourth thoracic vertebrae, bottom, middle, and top and establishing tags in step 305; locating the cranial aspect of the vertebral body of the 9th thoracic vertebrae, bottom, middle, top and establishing tags in step 306; using the assumption that spinal disks 4-9 are evenly spaced, the length of a single vertebral disk is calculated in step 307 and then compared to the lengths of the aforementioned tags and the VLAS and VHS are calculated from the tags in step 308.

Figure 4:
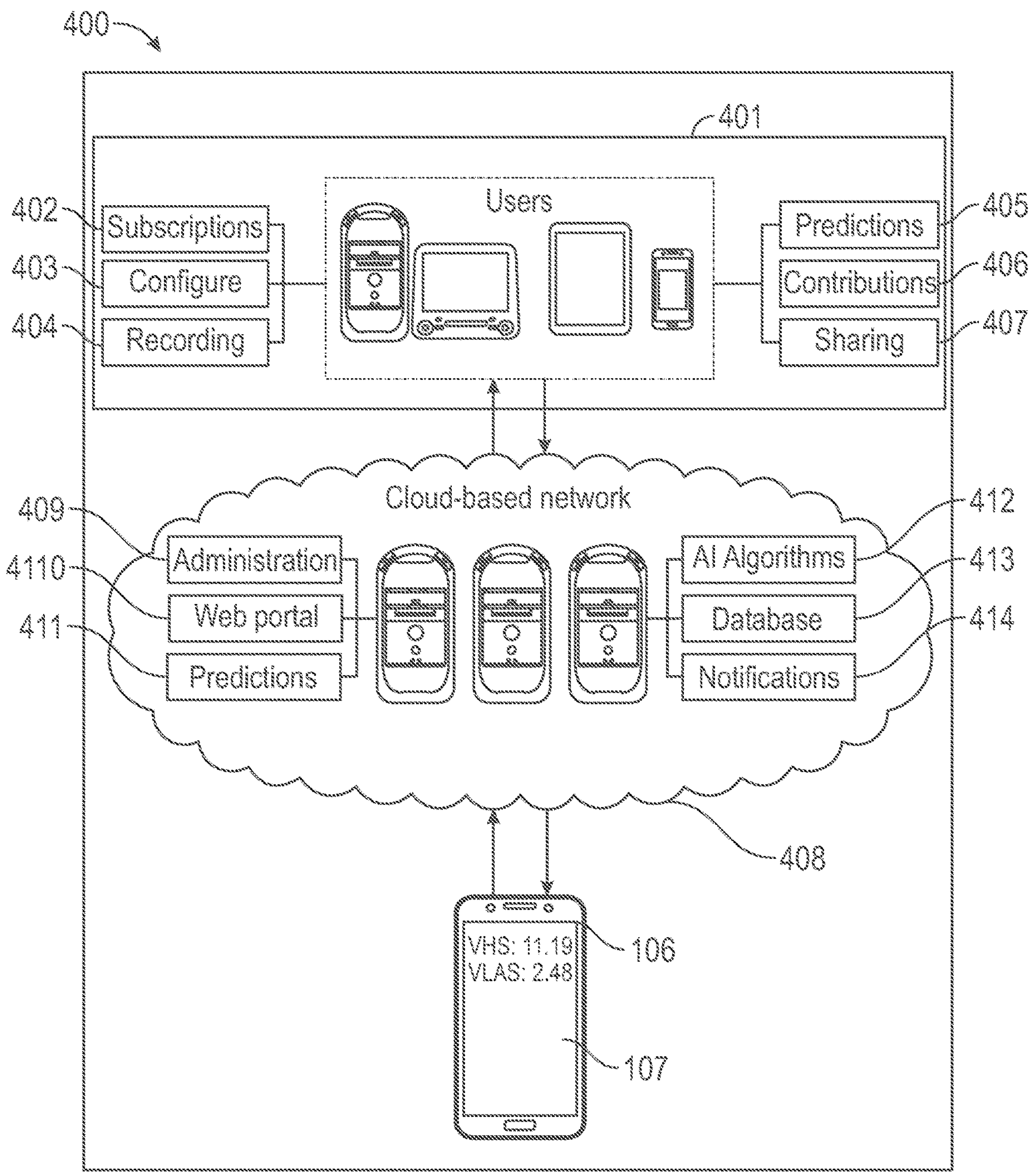
FIG. 4 shows the overall process operations of the system.

FIG. 4 shows the overall process operations 400 of the system 100 wherein, users 401 have functions that include but are not limited to selecting a subscription type 402; configuring their x-ray imaging software 403 to export compatible digital imagery; having the option to record 404 their benchmark tags for submission; contributing radiography images for VLAS and VHS 405; predicting VHS and VLAS 406; and sharing findings 407 with others via email, SMS, text messages and the like. The cloud network 408 is connected to the users through desktop software or an app and has operations that include but are not limited to administrative routines (user demographics, payments, subscription management, etc.); a web portal (an interface that allows image uploading and viewing prediction results, etc.); detailed prediction data (viewing statistics for each tag, downloading data, etc.); AI algorithms (CNN and RL, etc.); historical database (encrypted storage of imaging and all results); and stakeholder notifications (email, SMS, text messages, etc.). The digital device 106 running a mobile or online application 107 is connected to cloud network 402 which is connected with other users 401.

Figures 5, 6:
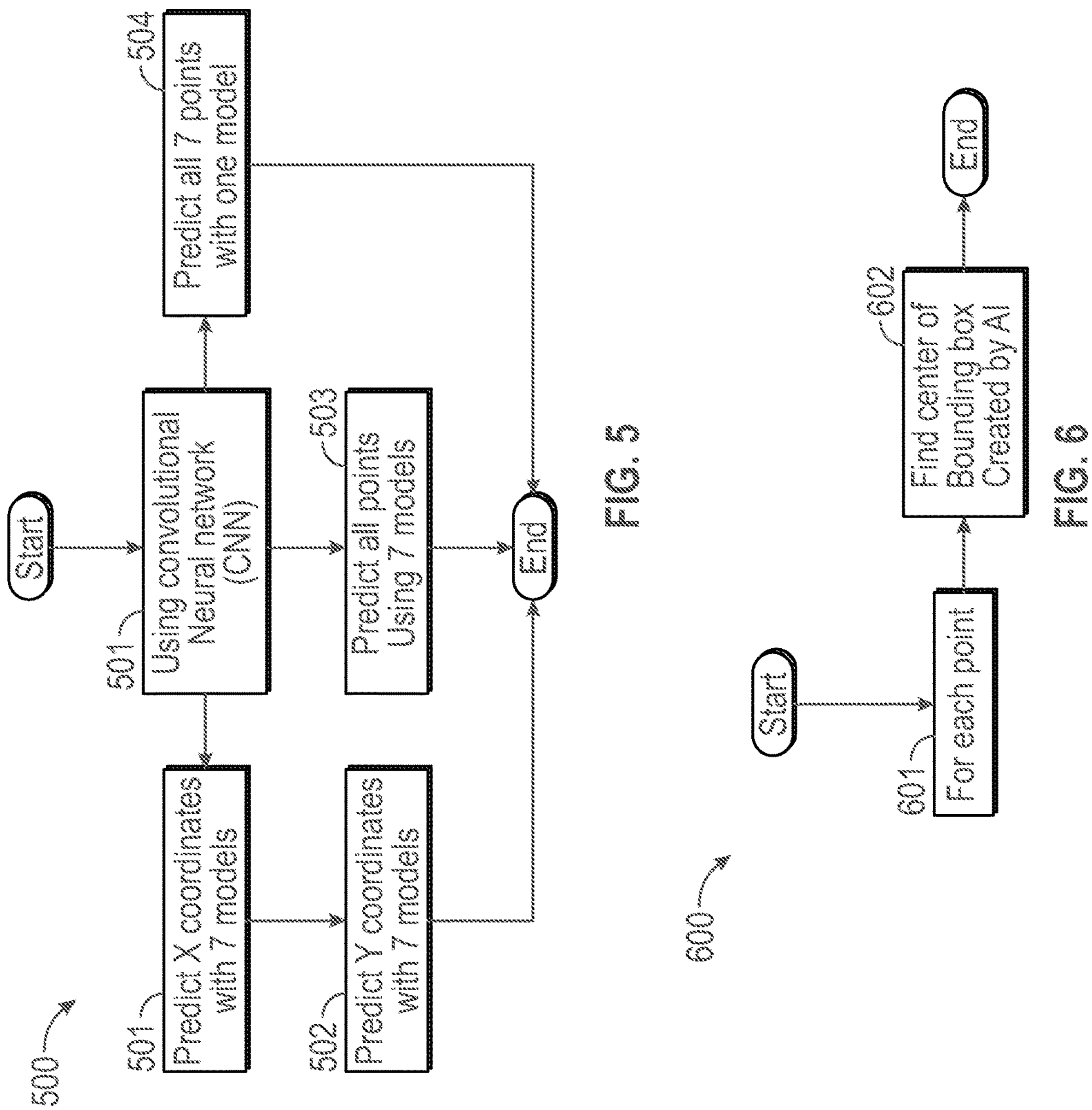
FIG. 5 shows a flow diagram of the CNN.
FIG. 6 shows a flow diagram of the bounding box.

FIG. 5 shows a flow diagram of the method of use of CNN algorithm 500, wherein seven models can be executed to predict accurate tag points. Said tag points are in both the X and Y directions. CNN algorithm 501 can predict accurate tag points by predicting X coordinates with 7 models in step 502, followed by Y coordinates with 7 models in step 502. In step 503, all points can be predicted by using 7 models. In step 503, all 7 points can be predicted by 1 model.

FIG. 6 shows a flow diagram of the bounding box prediction 600 wherein for each tag point 601 the center of the bounding box is generated by the AI 602.

Figure 7:
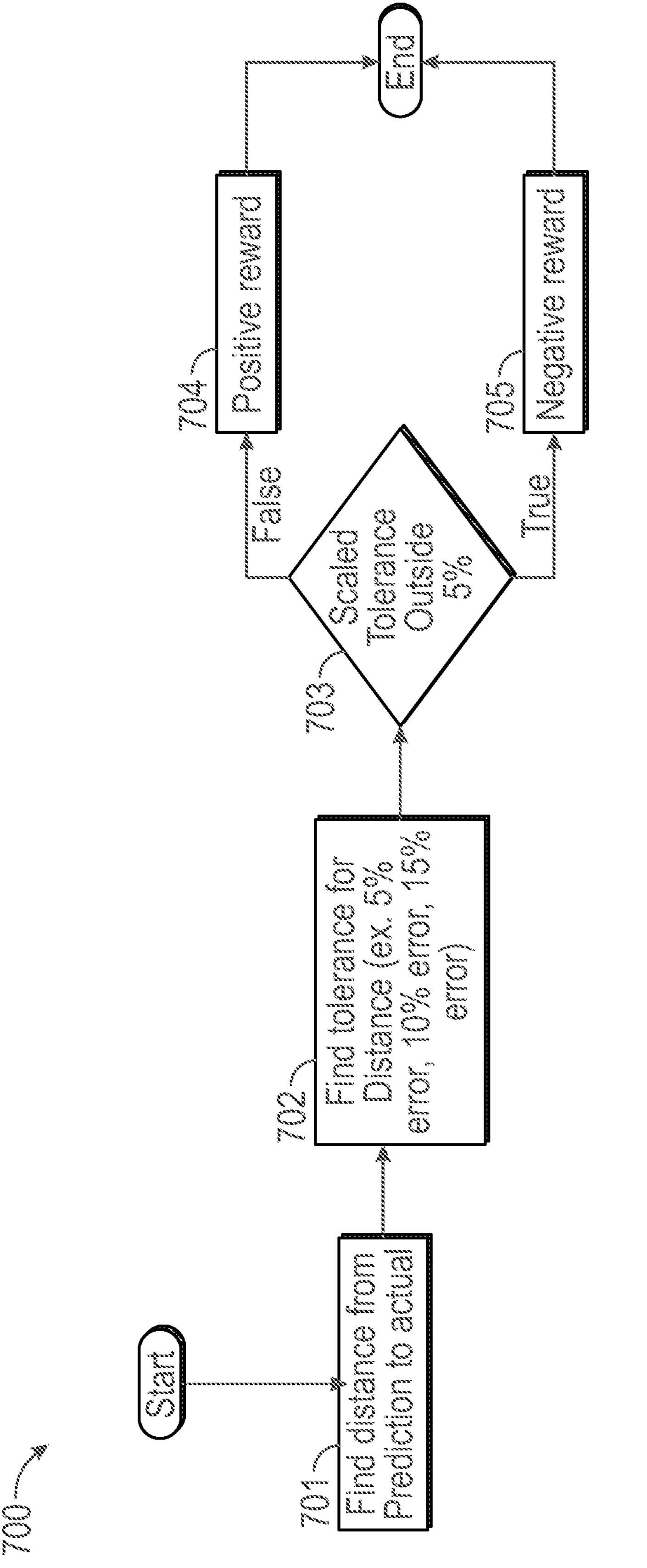
FIG. 7 shows a flow diagram of the rewards process.

FIG. 7 shows a flow diagram of the rewards process 700 as the AI determines the distance from an AI-predicted tag to the distance of a benchmark tag 701. After a percentage of error is determined 702, the program applies a positive reward 703 to the distance if it is within a 5% tolerance or a negative reward 704 if it is outside a 3% tolerance of said benchmark.

Figure 8:
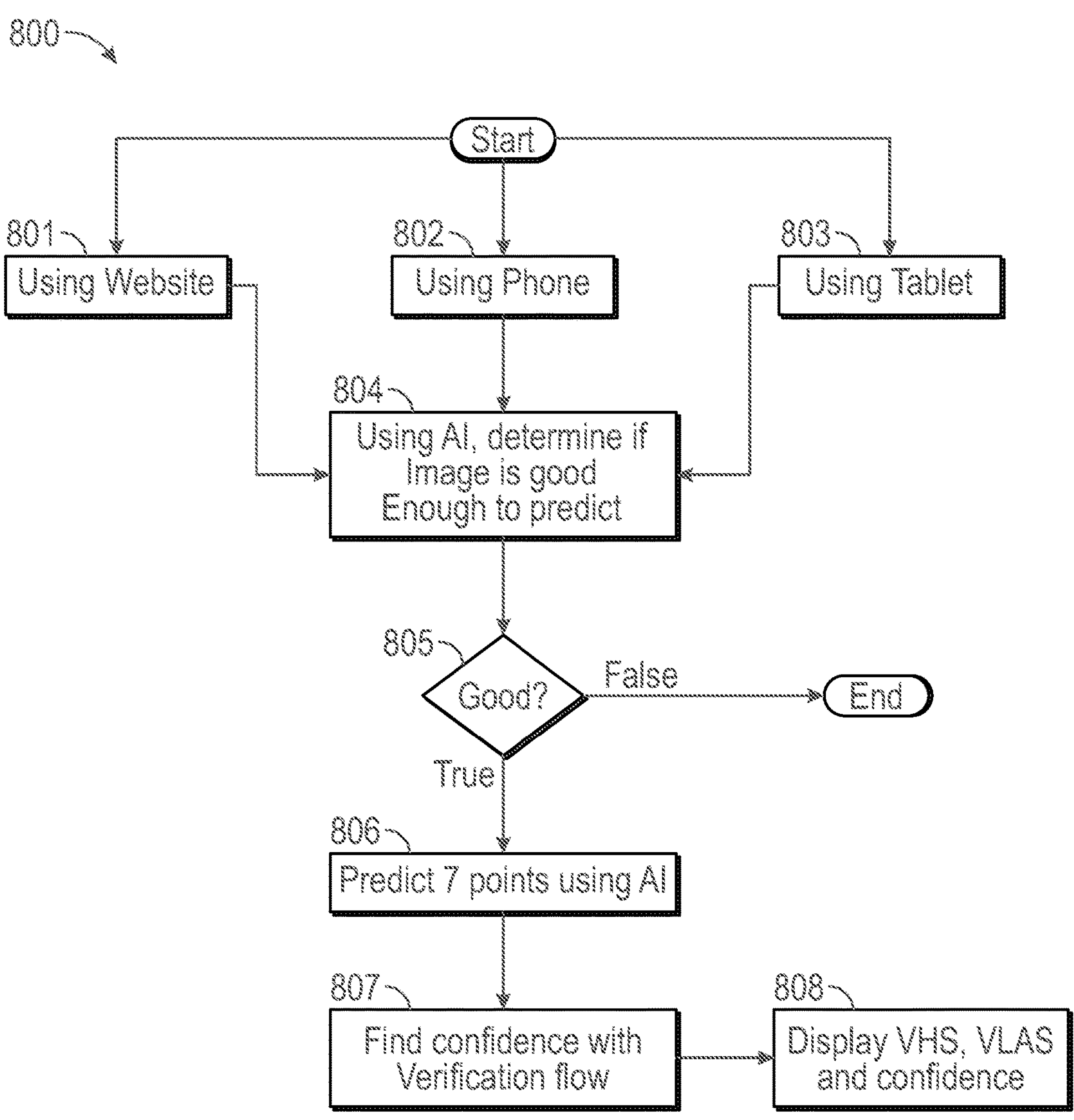
FIG. 8 shows a flow diagram of the predictive process.

FIG. 8 shows a flow diagram of the predictive process 800 that can be performed on a remote website 801, a phone 802 or a tablet 803, etc. Once an image is uploaded to these platforms, AI is used to determine whether the image is good enough for predicting 804, if the image is good 805 for predicting, at least seven tag points are predicted using AI 806, and confidence level is found for verification flow 807, VHS, VLS, and confidence level are displayed 808.

Figure 9:
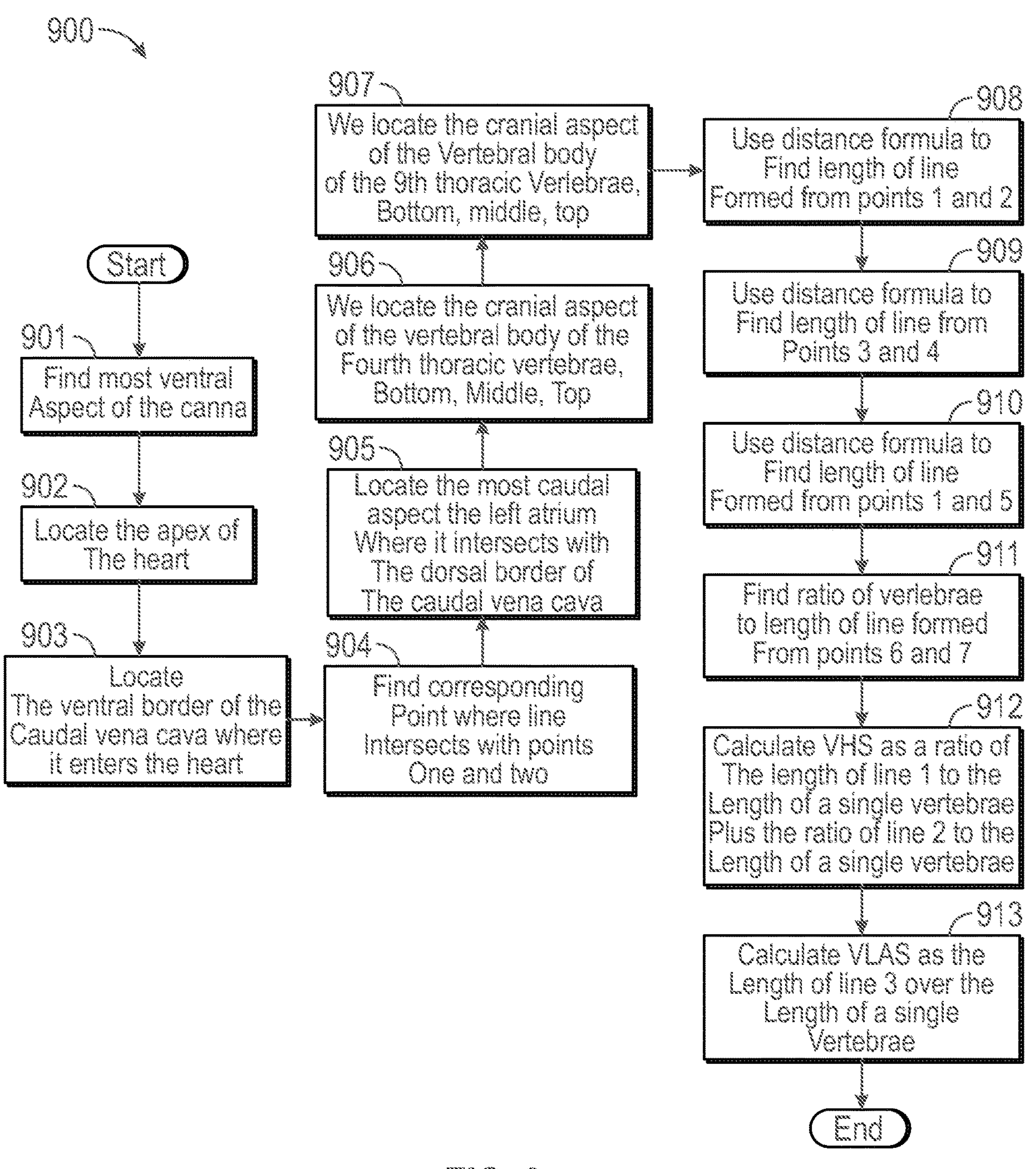
FIG. 9 shows a flow diagram of the tagging process.

FIG. 9 shows a flow diagram of the tagging process 900 wherein the catch point (tax) that is predicted is associated with the heart anatomy, for example, ventral aspect of the carina=point 1; apex of the heart=point 2, ventral border of the caudal vena cava=point 3, etc. The program applies a distance formula between each of the points and calculates the VHS and VLAS as a ratio of specifically associated line lengths that connect these points. In tagging process 900, step 901 includes finding the most ventral aspect of the carina, step 902 includes locating the apex of the heart, step 903 includes locating the ventral border of the caudal vena cava where it enters the heart, step 904 includes finding the corresponding point where the line intersects with points one and two, in step 905 includes locating the most caudal aspect of the left atrium where it intersects with the dorsal border of the caudal vena cava, in step 906 we locate the cranial aspect of the vertebral body of the fourth thoracic vertebrae, bottom, middle, top. Step 907, includes locating the cranial aspect of the vertebral body of the 9th thoracic vertebrae bottom, middle, and top. Step 908 includes using the distance formula to find the length of the line formed from points 1 and 2. Step 909 includes using the distance formula to find the length of the line formed from points 3 and 4. Step 910, includes using the distance formula to find the length of the line formed from points 1 and 5. Step 911, includes using the distance formula to find the length of the line formed from points 6 and 7. Step 912 includes VHS calculation as the ratio of the length of line 1 to the length of a single vertebra plus the ratio of line 2 to the length of a single vertebra. Step 913 includes VLS calculation based on the length of line 3 over the length of a single vertebra.

Figures 10, 11, 12:
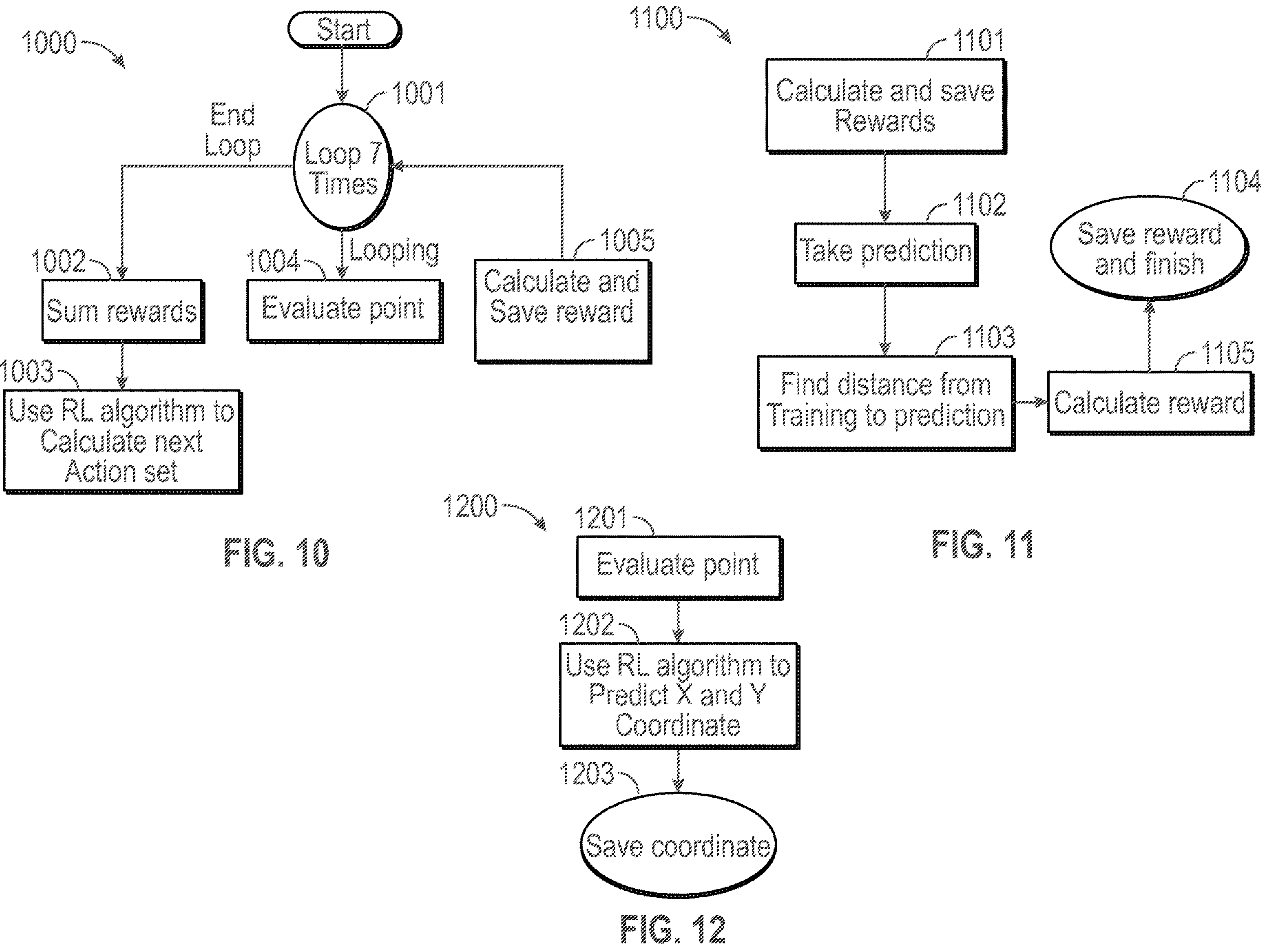
FIG. 10 shows a flow diagram of the rewards looping process.
FIG. 11 shows a flow diagram of the rewards calculation process.
FIG. 12 shows a flow diagram of the AI tagging process.

FIG. 10 shows a flow diagram of the rewards looping process 1000 whereby each verified point or tag is assigned a reward. Step 1001 includes a loop 7 times, step 1002 includes sum rewards after ending the loop, step 1003 includes using RL algorithm to calculate the next action set, step 1004 includes evaluating point in each loop of step 1001, followed by step 1005 includes calculating and saving reward before entering into the loop in step 1001.

FIG. 11 shows a flow diagram of the reward/s calculation process 1100. Step 1101 includes calculating and saving reward/s, step 1102 includes taking prediction, step 1103 includes finding the distance from training to prediction, step 1105 includes calculating reward/s, and step 1106 includes saving reward/s and finishing the process.

FIG. 12 shows a flow diagram of the AI coordinates tagging process 1200. Step 1201 includes evaluating the point, followed by step 1202 which includes using the RL algorithm to predict X and Y coordinates, followed by step 1203 which includes saving coordinates.

Figures 13, 14, 15:
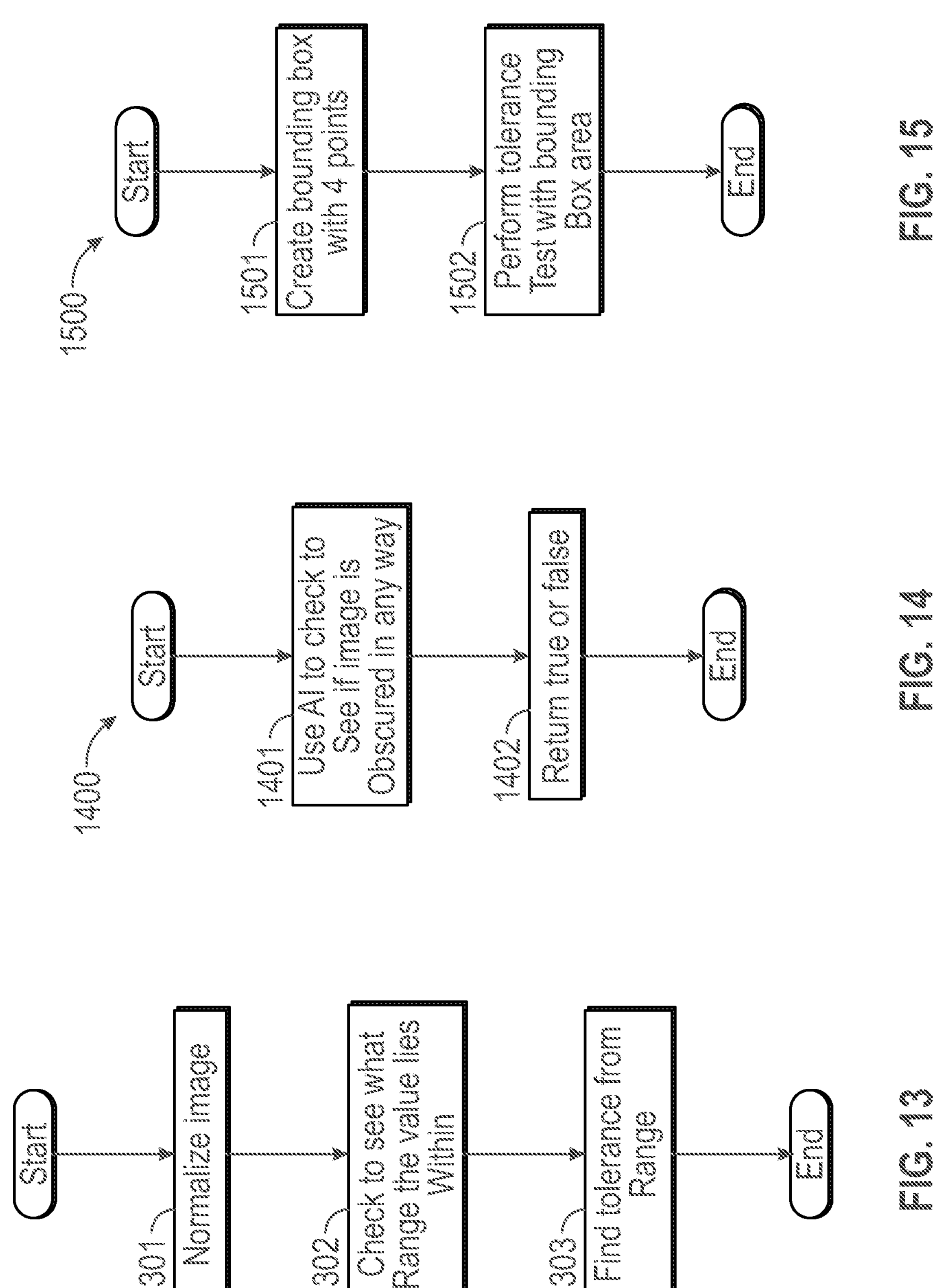
FIG. 13 shows a flow diagram of the image tolerance test process.
FIG. 14 shows a flow diagram of the image check process.
FIG. 15 shows a flow diagram of the tolerance test within the bounding boxes process.

FIG. 13 shows a flow diagram of the image tolerance test process 1300 which involves normalizing an image and determining an acceptable image tolerance range. Step 1301 includes normalizing the image, followed by step 1302 which includes checking to see the range value, followed by step 1303 which includes finding tolerance from the range.

FIG. 14 shows a flow diagram of the image check process 1400 and checking for any potential image obscurities. Step 1401 includes using AI to check for any obscurities in the image, followed by step 1402 which includes returning true or false for the presence of any image obscurities.

FIG. 15 shows a flow diagram of the tolerance test within the bounding boxes process based on four tag points 1500. Step 1501 includes creating a bounding box with 4 points, followed by step 1502 which includes performing a tolerance test with the bounding box area.

Figure 16:
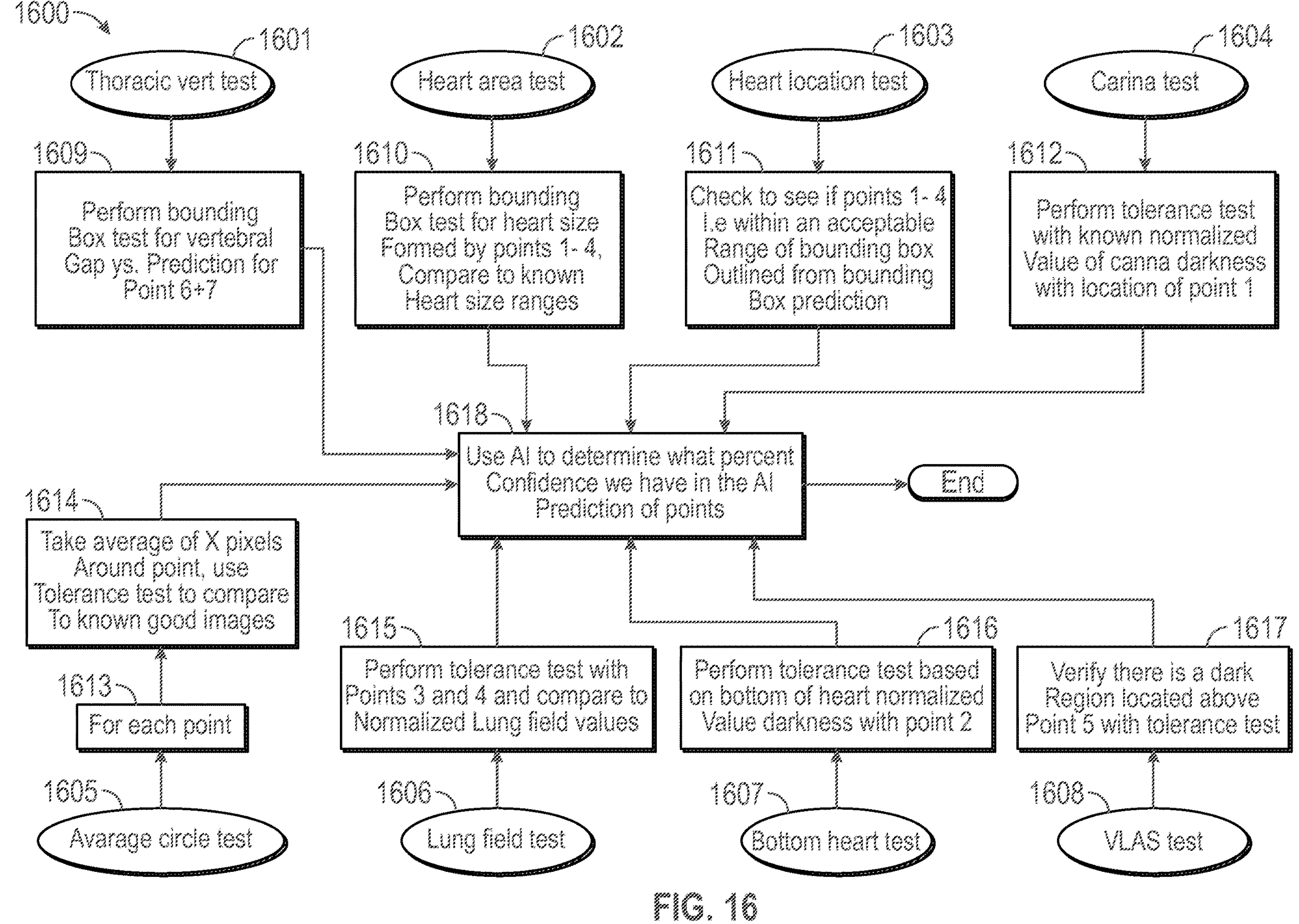
FIG. 16 shows a flow diagram of the AI prediction confidence process.

FIG. 16 shows a flow diagram of the AI prediction confidence process 1600 wherein every tag point that is recognized as a viable heart feature undergoes normalization, a bounding box test, and a tolerance test that allows the AI to make a confidence determination regarding their validity to predict VHS and VLAS. Using AI to determine what percent of confidence we have in AI prediction of points includes the following steps. Step 1601 includes the thoracic vertebra test which further includes step 1609 of performing a bounding box test for a vertebral gap against prediction for point 6 and 7. Step 1602 includes the heart area test which further includes step 1610 of performing a bounding box test for heart size formed by points 1 and 4 and comparing to known heart size ranges. Step 1603 includes a heart location test which further includes step 1611 of performing a bounding box test for heart location formed by points 1 and 4, and checking if they lie within an acceptable range of bounding box outline. Step 1604 includes a carina test which further includes step 1612 of performing a tolerance test with a known normalized value of carina darkness with the location of point 1. Step 1605 includes an average circle test which further includes step 1613 for each point of performing an average circle test by taking an average of pixels around the point, using a tolerance test to compare to known good images 1614. Step 1606 includes a lung field test which further includes step 1615 of performing a tolerance test for points 3 and 4 and comparing to normalized lung field values. Step 1607 includes a bottom heart test which further includes step 1616 of performing a tolerance test based on the bottom of heart normalized value darkness with point 2. Step 1608 includes a bottom heart test which further includes step 1617 of verifying the dark region located above point 5 with a tolerance test.

In view of the disclosure provided herein, a mobile application is created by techniques known to those of skill in the art using hardware, languages, and development environments known to the art. Those with skill in the art will recognize that mobile applications are written in several languages including, by way of non-limiting examples, C, C++, CA, Objective-C, Java™, JavaScript, Pascal, Object Pascal, Python™, Ruby, VB.NET, WML, and XHTML/HTML with or without CSS, or combinations thereof. The software is also compatible with a plurality of operating systems such as, but not limited to Windows™ Apple™, and Android™, and compatible with a multitude of hardware platforms such as, but not limited to personal desktops, laptops, tablets, smartphones, and the like. Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for the distribution of mobile applications including, by way of non-limiting examples, Apple App Store, Google Play, Chrome web Store, BlackBerry® App World, App Store for Palm devices, App Catalog for webOS, Windows® Marketplace for Mobile, Ovi Store for Nokia® devices, Samsung @ Apps, and Nintendo® DSi Shop.

In some embodiments, a computer program includes a standalone application, which is a program that is run as an independent computer process, not an add-on to an existing process, e.g., not a plug-in. Those with skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. The compilation is often performed, at least in part, to create an executable program. In some embodiments, a computer program includes one or more executable complied applications. In some embodiments, the computer program includes a web browser plug-in (e.g., extension, etc.). In computing, a plug-in is one or more software components that add specific functionality to a larger software application. Makers of software applications support plug-ins to enable third-party developers to create abilities that extend an application, to support easily adding no' features, and to reduce the size of an application. When supported, plug-ins enable customizing the functionality of a software application. For example, plug-ins are commonly used in web browsers to play videos, generate interactivity, scan for viruses, and display particular file types. Those with skill in the art will be familiar with several web browser plug-ins including, Adobes Flashy Player, Microsoft Silverlight®, and Apple® QuickTime®.

In some embodiments, the platforms, systems, media, and methods disclosed herein include software, server, and/or database modules, or use of the same. Given the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

The application of CNNs and RL to AI allows for deep learning of x-ray imaging to take place because the system incorporates a plurality of models and aggregates findings that have been shown to have a higher validity score. These higher validity scores (known as a reward) are then allowed to re-enter the learning knowledge base for deeper learning and continuous improvement of the system.

It is contemplated that the system of the present invention helps veterinarians and technicians to easily capture radiography imaging. The system includes a mobile application (app) that can be installed on a user's phone or tablet and can use onboard cameras to capture existing scans for inclusion into the system.

It is also contemplated and will be appreciated that the system of the present invention provides a means to accelerate the radiography process. Utilizing AI as a pre-screening method to rule out heart conditions can allow veterinarians to focus on other scans that may be of importance for a dog's survival. This greater efficiency can lead to less wait time for patients and reduced diagnosis and treatment costs.

It should also be appreciated that one of the unique features believed characteristic of the present application is that it facilitates overall improvements in canine VHS and VLAS diagnosis, as the system allows thousands of veterinarians around the world to contribute to AI learning, hundreds of thousands of canine breeds, types, ages, and sizes can be captured and included in the system. Therefore, veterinarians in one part of the world can benefit from contributions from other parts of the world.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as outlined in the description. Although the present embodiments are shown above, they are not limited to just these embodiments but are amenable to various changes and modifications without departing from the spirit thereof.

What is claimed is:

1. A method for predicting one or more of vertebral heart scale (VHS) and vertebral left atrial scores (VLAS) from canine radiography carried out by one or more digital devices comprising:

receiving one or more photographed canine radiography images, wherein the one or more photographed canine radiography images were captured using a camera on a mobile device to photograph one or more existing radiography images;

performing image localization and neural network pattern recognition by algorithmically determining one or more points of interest;

locating two or more positions on the one or more photographed canine radiography images, the two or more positions comprising a position on a ninth thoracic vertebrae;

comparing two or more lengths on the one or more photographed canine radiography images; and algorithmically generating a score, wherein the score is one or more of a vertebral heart scale score and a vertebral left atrial score, and wherein the score is based at least in part on the two or more lengths on the one or more photographed canine radiography images.

2. The method for predicting one or more of VHS and VLAS from canine radiography of claim 1, further comprising:

receiving tagging data from one or more veterinarians, wherein the tagging data corresponds to the one or more photographed canine radiography images; and generating one or more training points.

3. The method for predicting one or more of VHS and VLAS from canine radiography of claim 1, further comprising:

identifying and categorizing specific pixel colors based at least in part on the one or more photographed canine radiography images; and generating bounding boxes around the one or more points of interest.

4. The method for predicting one or more of VHS and VLAS from canine radiography of claim 1, further comprising:

performing reinforcement learning by:

establishing one or more bounding boxes corresponding to the one or more photographed canine radiography images;

performing one or more shaping functions; and assigning one or more rewards, wherein the one or more rewards are weighted based at least in part on the one or more shaping functions.

5. The method for predicting one or more of VHS and VLAS from canine radiography of claim 1, wherein at least one of the one or more digital devices is at least one server and at least one of the one or more digital devices is at least one user device, further comprising:

sending first data from the at least one server to the at least one user device;

displaying a web portal on the at least one user device;

displaying viewable statistics on the at least one user device; and sending second data from the at least one user device to the at least one server.

6. The method for predicting one or more of VHS and VLAS from canine radiography of claim 1, further comprising:

locating positions on the one or more photographed canine radiography images, the positions comprising:

a most ventral aspect of a carina;

an apex of a heart;

a most caudal aspect of a left atrium at which the left atrium intersects with a dorsal border of a caudal vena cava;

a cranial aspect of a vertebral body of a fourth thoracic vertebrae; and a cranial aspect of a vertebral body of the ninth thoracic vertebrae; and calculating a first length of at least one vertebral disk on the one or more photographed canine radiography images.

7. The method for predicting one or more of VHS and VLAS from canine radiography of claim 1, further comprising:

calculating a confidence level; and displaying the confidence level.

8. The method for predicting one or more of VHS and VLAS from canine radiography of claim 1, further comprising determining whether the one or more photographed canine radiography images are obscured.

9. A system of one or more digital devices for predicting one or more of vertebral heart scale (VHS) and vertebral left atrial scores (VLAS) from canine radiography comprising:

at least one server;

at least one processor;

at least one non-transitory computer-readable medium; and program instructions stored on the at least one non-transitory computer-readable medium that are executable by the at least one processor such that the system is configured to:

receive one or more photographed canine radiography images, wherein the one or more photographed canine radiography images were captured using a camera on a mobile device to photograph one or more existing radiography images;

perform image localization and neural network pattern recognition by algorithmically determining one or more points of interest;

locate two or more positions on the one or more photographed canine radiography images, the two or more positions comprising a position on a ninth thoracic vertebrae;

compare two or more lengths on the one or more photographed canine radiography images; and algorithmically generate a score, wherein the score is one or more of a vertebral heart scale score and a vertebral left atrial score, and wherein the score is based at least in part on the two or more lengths on the one or more photographed canine radiography images.

10. The system of one or more digital devices for predicting one or more of vertebral heart scale (VHS) and vertebral left atrial scores (VLAS) from canine radiography of claim 9, wherein the program instructions are executable by the at least one processor such that the system is further configured to:

receive tagging data from one or more veterinarians, wherein the tagging data corresponds to the one or more photographed canine radiography images; and generate one or more training points.

11. The system of one or more digital devices for predicting one or more of vertebral heart scale (VHS) and vertebral left atrial scores (VLAS) from canine radiography of claim 9, wherein the program instructions are executable by the at least one processor such that the system is further configured to:

identify and categorize specific pixel colors based at least in part on the one or more photographed canine radiography images; and generate bounding boxes around the one or more points of interest.

12. The system of one or more digital devices for predicting one or more of vertebral heart scale (VHS) and vertebral left atrial scores (VLAS) from canine radiography of claim 9, wherein the program instructions are executable by the at least one processor such that the system is further configured to:

perform reinforcement learning by:

establishing one or more bounding boxes corresponding to the one or more photographed canine radiography images;

performing one or more shaping functions; and assigning one or more rewards, wherein the one or more rewards are weighted based at least in part on the one or more shaping functions.

13. The system of one or more digital devices for predicting one or more of vertebral heart scale (VHS) and vertebral left atrial scores (VLAS) from canine radiography of claim 9, wherein at least one of the one or more digital devices is at least one server and at least one of the one or more digital devices is at least one user device, wherein the program instructions are executable by the at least one processor such that the system is further configured to:

send first data from the at least one server to the at least one user device;

display a web portal on the at least one user device;

display viewable statistics on the at least one user device; and send second data from the at least one user device to the at least one server.

14. The system of one or more digital devices for predicting one or more of vertebral heart scale (VHS) and vertebral left atrial scores (VLAS) from canine radiography of claim 9, wherein the program instructions are executable by the at least one processor such that the system is further configured to:

locate positions on the one or more photographed canine radiography images, the positions comprising:

a most ventral aspect of a carina;

an apex of a heart;

a most caudal aspect of a left atrium at which the left atrium intersects with a dorsal border of a caudal vena cava;

a cranial aspect of a vertebral body of a fourth thoracic vertebrae; and a cranial aspect of a vertebral body of a cranial aspect of a vertebral body of the ninth thoracic vertebrae; and calculate a first length of at least one vertebral disk on the one or more photographed canine radiography images.

15. The system of one or more digital devices for predicting one or more of vertebral heart scale (VHS) and vertebral left atrial scores (VLAS) from canine radiography of claim 9, wherein the program instructions are executable by the at least one processor such that the system is further configured to:

calculate a confidence level; and display the confidence level.

16. The system of one or more digital devices for predicting one or more of vertebral heart scale (VHS) and vertebral left atrial scores (VLAS) from canine radiography claim 9, wherein the program instructions are executable by the at least one processor such that the system is further configured to determine whether the one or more photographed canine radiography images are obscured.

17. A non-transitory computer-readable medium, wherein the non-transitory computer-readable medium is provisioned with program instructions that, when executed by at least one processor, cause one or more devices to:

receive one or more photographed canine radiography images, wherein the one or more photographed canine radiography images were captured using a camera on a mobile device to photograph one or more existing radiography images;

perform image localization and neural network pattern recognition by algorithmically determining one or more points of interest;

locate two or more positions on the one or more photographed canine radiography images, the two or more positions comprising a position on a ninth thoracic vertebrae;

compare two or more lengths on the one or more photographed canine radiography images; and algorithmically generate a score, wherein the score is one or more of a vertebral heart scale score and a vertebral left atrial score, and wherein the score is based at least in part on the two or more lengths on the one or more photographed canine radiography images.

18. The non-transitory computer-readable medium of claim 17, wherein the program instructions are executable by the at least one processor such that the one or more devices are further configured to:

receive tagging data from one or more veterinarians, wherein the tagging data corresponds to the one or more photographed canine radiography images; and generate one or more training points.

19. The non-transitory computer-readable medium of claim 17, wherein the program instructions are executable by the at least one processor such that the one or more devices are further configured to:

identify and categorize specific pixel colors based at least in part on the one or more photographed canine radiography images; and generate bounding boxes around the one or more points of interest.

20. The non-transitory computer-readable medium of claim 17, wherein the program instructions are executable by the at least one processor such that the one or more devices are further configured to:

perform reinforcement learning by:

establishing one or more bounding boxes corresponding to the one or more photographed canine radiography images;

performing one or more shaping functions; and assigning one or more rewards, wherein the one or more rewards are weighted based at least in part on the one or more shaping functions.

* * * * *